(12) United States Patent
Ruwart

(10) Patent No.: US 7,390,507 B2
(45) Date of Patent: Jun. 24, 2008

(54) COMPOSITIONS AND METHODS FOR THE TREATMENT OF RADIATION BURNS AND OTHER TRAUMATIC SKIN CONDITIONS

(76) Inventor: Mary J. Ruwart, 2455 Brathay Ct., Charlotte, NC (US) 28269

( * ) Notice: Subject to any disclaimer, the term of this patent is extended or adjusted under 35 U.S.C. 154(b) by 0 days.

(21) Appl. No.: 10/823,175

(22) Filed: Apr. 13, 2004

(65) Prior Publication Data

US 2005/0226945 A1    Oct. 13, 2005

(51) Int. Cl.
*A61K 35/60* (2006.01)
*A61K 36/00* (2006.01)

(52) U.S. Cl. .......................... 424/523; 424/725; 424/778
(58) Field of Classification Search ........................ None
See application file for complete search history.

(56) References Cited

U.S. PATENT DOCUMENTS

| 6,201,022 | B1 * | 3/2001 | Mease et al. | 514/560 |
| 6,579,543 | B1 * | 6/2003 | McClung | 424/728 |
| 2003/0007939 | A1 * | 1/2003 | Murad | 424/61 |
| 2004/0076695 | A1 * | 4/2004 | Gilbard | 424/765 |

* cited by examiner

*Primary Examiner*—Christopher R. Tate

(57) ABSTRACT

The present invention relates to compositions and methods for the treatment of traumatic conditions of the skin including radiation dermatitis, thermal burn, sunburn, dermatomyofibromas, and exposure-induced wrinkles, comprising omega-3 fish oils, tocopherols, lavender oil and a suitable amount of a pharmaceutically acceptable carrier, and optionally, one or more of the following: Sodium PCA, or MSM.

16 Claims, No Drawings

COMPOSITIONS AND METHODS FOR THE TREATMENT OF RADIATION BURNS AND OTHER TRAUMATIC SKIN CONDITIONS

FIELD OF THE INVENTION

The present invention relates to a composition comprising molecularly distilled omega-3 fish oils (eicosapentaenoic acid (EPA) and docosahexaenoic acid (DHA), gamma-linoleic acid, tocopherols, lavender oil, and a suitable amount of a pharmaceutically acceptable carrier, optionally including Sodium-2-pyrrolidone carboxylate or Methyl-Sulfonyl-Methane, or both, and methods for using the composition to treat traumatic conditions of the skin including radiation dermatitis, thermal burn, sunburn, dermatomyofibromas, and exposure-induced wrinkles.

BACKGROUND OF THE INVENTION

Fatty acids are essential for life. Besides storing energy, these fats are part of our makeup; they are formed in our healthy cells, muscles, nerves, and organs. The omega-3 polyunsaturated fatty acids are found in marine oils and are well known for their benefit as orally administered supplements for the maintenance of healthy arteries. A multitude of research has underscored the major role of essential fatty acids play as a defense against disease and age-related disorders. Gamma-linolenic acid (GHA) and docosahexaenoic acid (DHA) have been shown to protect against age related disorders such as heart disease, hypertension, elevated cholesterol, insulin resistance, dementia, memory loss, and atherosclerosis that can lead to heart disease, stroke, and elevated cholesterol levels. In youth, the fatty acids GLA, DHA, and eicosapentaenoic acid (EPA) are produced through metabolic processes involving the enzyme delta-6 desaturase. Unfortunately, this enzyme diminishes with age, leading to a deficiency of essential fatty acids that are needed to respond optimally to trauma.

In general, the "good" fats are unsaturated fats from oils of vegetables, nuts, and some fish. "Bad" fats are saturated fats, typically from animal fats, dairy products, etc. Without adequate levels of good fats, dangerous saturated fats will replace the essential fatty acids in our cells, reducing membrane fluidity and efficiency, starting the process of premature aging, and lessening the ability of the body to appropriately respond to trauma. Supplementation with the right proportions of fatty acids can maximize the production of anti-inflammatory prostaglandins (E1 and E3), while suppressing pro-inflammatory prostaglandin E2.

In addition, omega-3 fatty acids have been used as emulsion vehicles for the oral administration of poorly water-soluble therapeutic agents, as taught in U.S. Pat. No. 6,284,268, to Mishra. Their derivatives have been used to prevent a psychiatric, neurological or other central or peripheral nervous system disease, according to Horrobin, U.S. Pat. No. 6,479,544, who teaches a composition comprising EPA in combination with arachidonic acid or an arachidonic acid precursor such as dihomo-gammalinolenic (DGLA) or GLA. U.S. Pat. No. 6,361,806, to Allen, teaches the topical application of the linoleic acids, including gamma-linoleic acid, to the skin to effect changes in subcutaneous adipose tissue, and methods for ameliorating diseases of the subcutaneous tissue, primarily fibrocystic disease of the breast.

The variety of substances used to sooth irritated skin is limited only by the imagination of the formulator. Natural oils, such as aloe vera, are used extensively and several U.S. Patents are issued for specific formulas such as U.S. Pat. No. 6,193,987, to Harbeck, which teaches a lubricating composition for hands and skin comprised of organic safflower oil, flaxseed oil, tincture of benzoin, and organic beeswax blended in a cream-like base. U.S. Pat. No. 5,244,679, to Freston, teaches the alleviation of minor human skin irritations with topical application of glycerin, stearic acid, cocoa butter and boric acid blended together in a creamy base.

The omega-3 polyunsaturated fatty acids have also been sought as topical preparations, but technology in the field has had poor success in topical pharmaceutical formulations of fish oil-derived DHA and EPA. One of the main technical obstacles that has heretofore prevented their effective topical use is their very unpleasant smell, generated after application, and caused by oxidization of marine lipids from atmospheric oxygen and/or cutaneous enzymes.

The "off" or "rancid" odor associated with these oils is produced, in part, by oxidation of polyunsaturated fatty acids. Since highly unsaturated fatty acids occur in greater proportion in marine oils than in land animal- and vegetable-derived oils, rancidity is a greater problem when using marine sources. Oxidation of polyunsaturated fatty acids leads to the formation of hydroperoxides. The decomposition products of these hydroperoxides, such as aldehydes resulting from oxidation of marine animal oils, exhibit the unpleasant odors characteristic of rancid oils. Certain decomposition intermediates may also contribute to the problem.

Hence, the use of creams, lotions or gels containing omega-3 polyunsaturated fatty acids, which are initially odorless or pleasantly perfumed, is limited by their very unpleasant and repellent smell after application, which emanate from application sites and adhere to clothes that come into contact with them. As a result, consumer acceptability of topical compositions is low.

These odors appear to be characteristic of the fatty acids or long-chain hydrocarbons associated with natural oil compositions. In fish oils, for example, the "fishy" odor is postulated to be the result of interaction during oxidation between nitrogenous moieties and unsaturated glycerides present in the oil composition. Another theory regarding the source of the odor is that the unsaponifiable fraction (i.e., 5-hydrocarbon, sterol, methyl-sterol, long-chain alcohol, triterpene alcohol, pigment, trace materials and the like) of the oil composition is the component with which the "fishy" odor is associated.

In any event, this odor is not permanently removable even by drastic steam deodorization procedures (i.e., prolonged vacuum treatment at elevated temperatures, such as from about 230 degree to 260 degree. C.). The odor returns upon exposure of the "deodorized" oil to oxygen.

Since marine oils are capable of imparting advantageous properties to topical compositions, efforts have been made to overcome the aroma problem. These efforts were complicated by the fact that many processes alter the composition of fats and fatty acids. Exemplary processing techniques are refining, high temperature clay bleaching, high temperature-high pressure fat splitting, transesterification reactions and partial hydrogenation. Alterations arising from processing include cis-trans isomerization, conjugation of polyunsaturates, polymerization, dehydrogenation and the like.

Several strategies have emerged for using malodorous oils in topical compositions. In the first, only amounts of oil small enough not to adversely impact the odor of the complete topical composition were used. This strategy is not effective when higher concentrations of oil are required or desirable. The use of perfumes or any other deodorizing agent, even if intense and strong, is useless. In fact, upon application of the cream or of any other topical form to the skin, the perfume volatile components evaporate faster than the higher boiling esters of polyunsaturated fatty acids, which assume, in a very short time, a very unpleasant smell.

U.S. Pat. No. 5,472,705, to Bruzzese, teaches the addition of phenolic antioxidants to topical compositions of the esters of omega-3 polyunsaturated fatty acids to hinder the decomposition and the generation of very unpleasant and repellent smells. Horrobin, in U.S. Pat. No. 6,479,544, provides an example for topical use of EPA with GLA, but neither addresses the problem of odor in a topical composition, discloses the addition of DHA or lavender oil to the EPA-GLA composition, nor teaches the need to use molecularly distilled fish oils in the specific proportions with GLA that are appropriate for topical administration.

U.S. Pat. No. 5,650,157, to Bockow, teaches a method to prepare stable, deodorized oils by adding an amount of a deodorizing agent effective to substantially reduce the odor of the derived oil composition, fraction or combination thereof. Bockow teaches a multi-step process for the deodorization of marine oils wherein warm water is added to ground raw marine product, the pH is adjusted by the addition of acid to between 2.0 and 3.5, preferably about 2.8, the solution is mixed gently and allowed to stand at room temperature for approximately 24 hours to allow the oil to separate. Following this, the solution is mixed and allowed to stand again two or three times, requiring several days for the preparation of the deodorized oils. After the oil is drawn off, particles are removed, and the oil is filtered, heated, and allowed to cool gradually.

U.S. Pat. No. 6,551,602, to Barrett teaches a conjugated linoleic acid composition containing a phenolic compound selected from the group consisting of epigallocatechin gallate, genistein, green tea extract and soy extract as a treatment for wrinkles.

Unexpectedly, this inventor has discovered that the use of molecularly distilled fish oils to supply EPA and DHA diminishes the generation of unpleasant smells and the need for phenolic antioxidants as taught by Bruzzese. The molecularly distilled fish oils, in a specific proportion of fish oils with GLA, mixed tocopherols, and lavender oil, were found to have remarkable success in treating traumatic conditions of the skin.

Radiation Dermatitis

Radiation therapy has traditionally been the treatment of choice for locally or regionally advanced cancer, but its therapeutic efficacy is often hindered by limited tolerance of normal tissues and by tumor radio resistance. To improve therapeutic outcome, radiotherapy is frequently combined with chemotherapeutic drugs that are themselves cytotoxic and may sensitize cells to radiation. Milas L, et al, 17 (5 Suppl 5) ONCOLOGY (Hunting) 15-24 (2003). Radiation may cause severe burns of the skin and surrounding tissue as well as permanent changes in pigmentation. As many as 95% of patients treated with radiation therapy for cancer will experience a skin reaction. Porock D, Nikoletti S, Kristjanson L 19(4) PLAST SURG NURS. 185-92 (1999).

Some patients suffer radiation-induced skin injuries and younger patients may face an increased risk of future cancer. Davis MM, et al 20(4) J AM ACAD DERMATOL 608-16 (1989). Interventionists are suffering injury and are exposing their staff to high doses of radiation. In some interventional procedures, skin doses to staff approach those experienced in some cancer radiotherapy fractions. Radiation-induced skin injuries occur in patients due to the use of inappropriate equipment and, more often, poor operational technique. Valentin, 30(2) J. ANN ICRP, 7-67 (2000). Others report that such burns, when experienced in the hand, require aggressive debridement and immediate coverage with well-vascularized flaps, either regional or free-tissue transfers to achieve adequate wound healing and the most rapid, effective return of function with rapid institution of therapeutic modalities. Milanov NO, Shilov BL, Tjulenev AV 92(2) PLAST RECONSTR SURG. 294-300(1993).

Aloe vera has been tried without improvement in the results of irradiated breast tissue, Heggie S, et al, 25(6) CANCER NURS. 442-51 (2002), as has topical Vitamin C, Halperin EC, et al, 26(3) INT J RADIAT ONCOL. BIOL. PHYS 413-6 (1993). Other groups report that prophylactic and ongoing use of topical therapy with either topical corticosteroid or a dexpanthenol-containing emollient ameliorates, but does not prevent, radiation dermatitis. Schmuth, M, et al 146(6) BR J DERMATOL. 983-91(2002). Similarly, the increased effectiveness produced by the addition of a potent topical corticosteroid to an emollient cream is statistically significant as compared to the emollient cream itself in reducing acute radiation dermatitis but had no effect on pigmentation changes. Bostrom, A, et al, 59(3) RADIOTHER ONCOL. 257-65 (2001). Authors report that moist skin care with 3% urea lotion delays the occurrence and reduces the grade of acute skin reactions in percutaneously irradiated patients with head and neck tumors. Momm, F, et al, 179(10) STRAHLENTHER ONKOL. 708-12 (2003).

Biafine and Lipiderm had no radioprotective effect, Fenig E, 8(2) ONCOL. REP 305-9 (2001), while another group reported a significant dermato-cytoprotective effect of amifostine in its retrospective analysis. Kouvaris, J, 12(5) EUR J DERMATOL. 458-62 (2002).

Misoprostol, a prostaglandin E(1) analog, has been found to be an effective radioprotector in animal studies. It was shown to prevent to oncogenic transformation of Syrian hamster embryos exposed to radiation in utero. LaNasa P, 29(2) INT J RADIAT ONCOL. BIOL. PHYS. 273-5 (1994). However, results in humans were disappointing. Oral complications of radiation therapy seriously impact quality of life because of changes in taste, saliva, mucous, and eating. Johnson D J, et al, 54(5) INT J RADIAT ONCOL. BIOL. PHYS 1455-9 (2002). Oral administration of misoprostol produced inconsistent results in the prevention of oral mucositis in head and neck cancer patients treated with radiation. Hanson W R, et al 2(11) AM J THER. 850-857 (1995).

Recent advances in molecular biology have discovered many cellular molecules, including the cyclooxygenase-2 (COX-2) enzyme, which promote tumor cell survival and are responsible for tumor resistance to cytotoxic agents, that are being studied as potential targets for augmentation of response to radiation or chemotherapy. Milas L, et al, 17 (5 Suppl 5) ONCOLOGY (Hunting) 15-24 (2003)

None of the attempted treatments is completely successful and there is no "gold standard" in the prophylaxis and treatment of radiation dermatitis, creating a long-felt need to treat the dermatologic effects of radiation.

Burns

Usually the result of trauma, but occasionally due to self mutilation, burns are amongst the most serious conditions seen by medical personnel. Treatment is supportive, with antibiotics and fluid replacement followed by multiple skin grafting to restore the appearance as best as can be accomplished. The hypermetabolic response, which is mediated by hugely increased levels of circulating catecholamines, prostaglandins, glucagon and cortisol, causes profound skeletal muscle catabolism, immune deficiency, peripheral lipolysis, reduced bone mineralization, reduced linear growth, and increased energy expenditure. Murphy K D, Lee J O, and Herndon D N, 4(3) EXPERT OPIN PHARMACOTHER. 369-84 (2003). Burn-related immune disturbances, specifically the burn-related suppression of mesenteric lymph node T-cell proliferation and interleukin-2 production, were studied in rats and prevented when the rats were fed on a high-protein diet rich in glutamine, arginine, fish oil, and nucleotides. Choudhry, M A, 31(6) CRIT CARE MED 1764-70 (2003)

Topical treatments for the traumatic conditions produced by burns has not been remarkable. Jandera, et al, 26(3) BURNS 265-70 (2000) reported more rapid healing in both the *Melaleuca alternifolia* Hydrogel and water-cooled burns compared with the untreated controls. Tea tree oil, a known antiseptic, was ineffective in inhibiting bacterial growth in burns and therefore not recommended after clinical trial. Faoagali J, George N, Leditschke J F. 23(4) BURNS 349-51 (1997).

Sunburn

Sunburn is produced by the ultraviolet (UV) radiation of the sun and is mediated by inflammatory substance cyclooxygenase-2 and prostaglandins. Cyclooxygenase-2 expression is induced by ultraviolet irradiation; data suggest that tyrosine kinases and reactive oxygen intermediates are involved in this induction. Isoherranen, K, et al, 140(6) BR J DERMATOL 1017-22 (1999). The effects of ultra-violet radiation of the sun can be mitigated by oral supplementation with dietary fish oils. Following 3 months of fish oil, prostaglandin E2 decreased in both control and irradiated skin. Reduction of UV-induced trauma by fish oil may be due, at least partially, to lowered prostaglandin E2 levels. The photoprotection against UVA-provocation of a papular response suggests a clinical application for fish oil in polymorphic light eruption. Rhodes, L E, et al 105(4) J INVEST DERMATOL 532-5 (1995).

Exposure-Induced Wrinkles

Numerous measures have been attempted to retard the natural aging process of the human skin, which is greatly exacerbated by trauma, e.g. sunburn and windburn. The fashionable treatment of the day is the injection of Botulinum toxin to weaken the smooth muscle around the wrinkle and cause it to collapse, popularized as "Botox." Redaelli, A, Forte, R, 5(3-4) J COSMET LASER THER 220-2 (2003). But other aggressive therapies are readily available, limited only by the courage of the recipient. Pyruvic acid peels, Ghersetich, I, 30(1) DERMATOL SURG 32-6 (2004), injectable collagen, Galadari H, Lebwohl M, 49(5 Suppl) J AM ACAD DERMATOL. S265-6 (2003), and laser skin resurfacing, Batra R S, 139(10) ARCH DERMATOL 1295-9 (2003), have all been used with mixed success and obvious risks.

There is a suggestion that gentler methodology may be as effective as injections and chemical peels. French researchers reported some success in the use of a preparation containing a fucose-rich polysaccharide as an active principle on the microdepressionary skin surface. In 17 out of 20 female volunteers, aged from 39 to 71 years, exhibited significant improvement of the skin surface relief after 4 weeks of treatment, as shown by the displacement of geometrical characteristics, towards a "younger" pattern, corresponding to a decrease of apparent age by 10-15 years. Robert C, Robert A, and Robert L, 51(10) PATHOL BIOL(PARIS) 586-90 (2003). Alpha-Lipoic Acid has also been demonstrated to have some effect, Beinter, H, 149(4) BR J DERMATOL 841-9 (2003), and is now found in a multitude of preparations available at any local pharmacy or supermarket.

Dermatomyfibroma

Dermatomyfibroma is a recently described, rare, benign proliferation of myofibroblasts of the skin, often as a reaction to minor trauma such as scratches and insect bites, mainly found in young women. Only a few cases have been reported in males, but a case was reported in a four year old boy. Rose C, Brocker E B, 16(6) PEDIATR DERMATOL 456-9 (1999). Treatment is generally by conservative excision; follow-up information revealed no evidence of recurrence. Kamino, H, 19(2) J CUTAN PATHOL 85-93 (1992). Occasionally, lesions can be resolved through prompt and frequent topical application of steroid cream or diphenhydramine.

SUMMARY OF THE INVENTION

The need exists for a topical treatment for traumatic conditions of the skin including radiation dermatitis, superficial burn, sunburn, dermatomyofibromas, and exposure-induced wrinkles. Unexpectedly, this Inventor has discovered that direct topical application of the right proportions of molecularly distilled gamma-linoleic acid (GLA), eicosapentanoic acid (EPA) and docosahexaenoic acid (DHA) can help improve response to trauma by modulating the complex prostaglandin cascade. The composition of this invention further comprises one or more tocopherols selected from the group consisting of alpha-tocopheryl acetate, alpha-tocopherol, and mixed tocopherols; lavender oil; and a suitable amount of a pharmaceutically acceptable carrier. The composition may optionally include Sodium-2-pyrrolidone carboxylate or Methyl-sulfonyl-Methane, or both. The advantages of this invention are its remarkable clinical success in the treatment of traumatic conditions of the skin and the ease of preparation. The compositions require no elaborate and protracted separation procedures but are prepared by mixing the components, immediately after which the compositions may be applied topically to the affected skin.

DETAILED DESCRIPTION OF THE INVENTION

Definitions:

The omega-3 polyunsaturated fatty acids are generally prepared from fish oil (EPA and DHA) or borage oil (GLA) and are available from numerous pharmaceutical and nutraceutical wholesalers and retailers. In a specific embodiment of the invention, gamma-linoleic acid and docosahexaenoic acid are obtained from "Super GLA/DHA" capsules sold by the Life Extension Foundation of Fort Lauderdale, Fla. for oral supplementation. Eicosapentanoic acid (EPA) and docosahexaenoic acid (DHA) are obtained from "Omega 3" molecularly distilled fish oil sold by ZonePerfect Nutrition Co., of Beverly, Mass.

Vitamin E is a mixture of tocopherols. D-alpha-tocopherol has the highest biological activity and is the most widely available form of vitamin E in food. Vegetables and seed oils including soybean, safflower and corn, sunflower seeds, nuts, whole grains, and wheat germ are the main sources of the tocopherols. Meydani, 345(8943) LANCET 170-75 (1995). The other isomers (beta, gamma, and delta) are less biologically active than d-alpha-tocopherol. The commercially available synthetic forms of vitamin E comprise an approximately equal mixture of eight stereoisomeric forms of alpha-tocopherol. For practical purposes, 1 international unit (IU) of vitamin E is referred to as 1 mg of the synthetic form, racemic alpha-tocopheryl acetate, and the natural form of d-alpha-tocopherol has a biopotency of vitamin E equal to 1.49 IU. Vitamin E may be obtained from numerous nutraceutical wholesalers and retailers and in a specific embodiment, "Jason's Vitamin E oil," sold by the Life Extension Foundation of Fort Lauderdale, Fla., is used to supply d-alpha tocopherol. Mixed tocopherols are supplied by "Gamma E Tocopherol/tocotrienols" also sold by Life Extension Foundation.

Pharmaceutically acceptable carriers are selected from those well known to those of ordinary skill of the art including, but not limited to, those listed in reference texts such as REMINGTON'S PHARMACEUTICAL SCIENCES 16th Edition, Mack Publishing Company 1980, Ed. A. Osol and are readily available from wholesalers well known to those of ordinary skill in the art.

According to the invention, the pharmaceutically acceptable carrier may be selected from the group consisting of cocoa butter, aloe vera gel, aquafor, petroleum jelly, lecithin, almond oil, borage oil, canola oil, grape seed oil, jojoba oil, olive oil, soybean oil, sunflower oil, wheat germ oil, apricot kernel oil, carrot oil, coconut oil, mango butter, evening primrose oil, black currant oil, avocado oil, microcrystalline wax, paraffin, petrolatum, petroleum jelly, ozokerite, montan wax, beeswax, lanolin or a derivative, candelilla wax, ouricury wax, carnauba wax, Japan wax, cocoa butter, sugarcane wax, cork fiber wax, and mixtures thereof.

In a specific embodiment of the invention, the pharmaceutically acceptable carrier is cocoa butter. Cocoa butter may be used as Palmer's® Cocoa Butter Lotion #4180, obtained from E.T. Browne Drug Co., Inc., of Englewood Cliffs, N.J.

Lavender Oil is sold by retailers such as Young Living Essential Oils of Lehi, Utah. Lavender was used historically as a condiment and for flavoring dishes to comfort the stomach. It has aromatic, carminative and nervine properties and has been reported to soothe burns and encourage tissue repair. Though largely used in perfumery, it is now not much employed internally, except as a flavoring agent, occurring occasionally in pharmacy to cover disagreeable odors in ointments and other compounds. Lavender lozenges are employed both as a mild stimulant and for their pleasant taste. Lavender stems, growing 1 or 2 feet high, are gray-green and angular, with flaking bark. The gray-green leaves are opposite, sessile, downy, and lanceolate to oblong-linear. The lilac-colored, tubular flowers are arranged in successive whorls up the stem. The fragrant oil from the lavender flowers is a valuable article of commerce, much used in perfumery, and to a lesser extent in medicine. The fine aromatic smell is found in all parts of the shrub, but the essential oil is only produced from the flowers and flower-stalks.

Sodium-2-pyrrolidone carboxylate (Sodium PCA) may optionally be used and is sold by retailers such as Twin Laboratories, Inc., of Hauppauge, N.Y. and in bulk by wholesalers such as Thinker Chemical Company, Ltd., of Hangzhou 310018, China. Sodium PCA is a naturally-occurring hygroscopic (water-attracting) component of human skin that has become an important moisturizing additive in skin-care and hair-care cosmetics in the recent years for its stronger hydrating power than that of glycerin, sorbitol and propanediol.

Methyl-Sulfonyl-Methane may be optionally used, is sold by numerous retailers and bulk distributors such as What Medicine of Hampshire, U.K. Methy-sufonyl-methane (MSM), and is an odorless, virtually tasteless, white crystalline substance. The key portion of MSM is the sulfur component. Sulfur is necessary for the proper formation of proteins. One of the essential components in all life forms, sulfur is involved in amino acid production, connective tissue, skin, hair, nails, (in animals, hide and hooves), enzymes, hormones, and immunoglobulins. It is available as a powder that can be ingested orally or easily be combined with a pharmaceutically acceptable carrier into a topical cream.

Compositions

The present invention relates to compositions for soothing traumatic conditions of the skin comprising the molecularly distilled omega-3 fish oils eicosapentanoic acid (EPA) and docosahexaenoic acid (DHA), with the addition of gamma-linoleic acid (GLA), in specific proportions by weight; one or more tocopherols selected from the group consisting of alpha-tocopheryl acetate, alpha-tocopherol, and mixed tocopherols; lavender oil; and a suitable amount of a pharmaceutically acceptable carrier. The compositions protect against these traumatic skin conditions with remarkable success.

The specific proportions of the omega-3 oils that have produced unexpected success in treating traumatic conditions of the skin are: GLA in an amount ranging from about 10% to about 40%, EPA in an amount ranging from about 20% to about 60%, and DHA in an amount ranging from about 20% to about 60%. A practitioner skilled in the art will select the appropriate blend within those ranges without undue experimentation. In a more specific embodiment of the composition, GLA is present in an amount ranging from about 15% to about 30%, EPA is present in an amount ranging from about 30% to about 50%, and DHA is present in an amount ranging from about 30% to about 50%. In the most specific embodiment, GLA is present in an amount of about 20% by weight, EPA is present in an amount of about 40% by weight, and DHA is present in an amount of about 40% by weight. The total weight of the molecularly distilled omega-3 fish oils is up to about 3000 mg, specifically, between about 500 mg and about 2000 mg, and most specifically, about 1000 mg, in about 120 ml of pharmaceutically acceptable carrier.

In a specific embodiment of the invention, tocopherol is present in an amount between about 1000 IU and about 15000 IU, and lavender oil is present in an amount up to about 1 mg, specifically up to about 600 mcg, and most specifically up to about 300 mcg, in about 120 ml of pharmaceutically acceptable carrier.

In a specific and most preferred embodiment of the composition, GLA is present in an amount of about 150 mg; EPA is present in an amount of about 320 mg; DHA is present in an amount of about 380 mg; tocopherol is present in an amount of about 5600 IU, and lavender oil is present in an amount of about 300 mcg, in about 120 ml of pharmaceutically acceptable carrier.

In a specific embodiment, the tocopherol is alpha-tocopheryl acetate and mixed tocopherols; and the pharmaceutically acceptable carrier is cocoa butter. Optionally, the composition may contain Sodium PCA in an amount up to 1 g, specifically 0.5 g and most specifically 0.25 g, Methyl-Sulfonyl-Methane, in an amount of about 6 g to about 18 g, preferably about 9 g to about 15 g and most specifically 12 g, or both Sodium PCA and Methyl-Sulfonyl-Methane.

The basic composition is prepared by weighing and measuring the ingredients to be used, combining them, and mixing them gently until a smooth, creamy consistency is obtained. Sodium PCA and Methyl-Sulfonyl Methane may be dissolved or mixed in an appropriate carrier prior to addition to the cream.

Also provided are topical compositions as described herein characterized in that it is active against traumatic conditions of the skin, specifically radiation dermatitis, thermal burns, sunburn, exposure-induced wrinkles, and dermatomyofibromas.

Methods of Treatment

The invention further provides methods of treating traumatic conditions of the skin of a human by topically treating the skin with the composition described in this invention.

Exemplary ailments which may be treated using a topical composition of the present invention in admixture with a pharmaceutically active agent are radiation dermatitis, thermal burns, dermatomyofibromas, bursitis, tendonitis, epicondylitis, myofacial pain syndrome, myositis, degenerative and arthritis, vasospastic disorders, neck pain, lower back pain, sciatica, post exercise pain, post operative swelling, burns, diaper rash, itching, acne, sunburn, windburn, fever blister, cold sore, insect bite, insect sting, poison ivy, poison oak, poison sumac, anorectal disorders, dermatitis, such as seborrheic dermatitis, psoriasis, fungus, other skin conditions, such as some types of skin discoloration, ophthalmic disorders, and the like. Most specifically, the topical composition is used to treat radiation dermatitis, thermal burns, sunburn, and dermatomyofibromas. A topical composition of the present invention may also be used to prevent and reduce exposure-induced wrinkles.

Specifically, treatment of radiation dermatitis according to the invention is performed by topical application of the compositions of the invention to the affected area immediately after radiation treatments and is repeated from once to three times daily through out the course of radiation, specifically twice daily.

Specifically, treatment of superficial burn according to the invention is performed by topical application of the compositions of the invention to the affected area immediately after the burn is experienced and repeated from one to three times daily until the skin heals.

Specifically, treatment of dermatomyofibromas according to the invention is performed by topical application of the compositions to the lesions as soon as a new lesion is noted and repeated from one to five times daily until the skin heals, specifically three times daily, until the skin heals.

Specifically, prevention and treatment of exposure-induced wrinkles according to the invention is performed by topical application of the compositions of the invention to the skin prior to exposure, e.g., wind, sun, and after exposure one to three times daily as needed.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

The present example relates to a specific embodiment of the composition of the invention. The specific ingredients are 120 ml of Palmer's Cocoa Butter Lotion #4180; 5 drops (300 micrograms) of Young Living's Lavender Oil; the contents of 1 capsule of Life Extension's GLA/DHA containing 153 mg gamma linoleic acid (GLA) and 167 mg of docosahexaenoic acid (DHA); the contents of 2 capsules of Life Extension's Gamma E with tocotrienols, mixed tocopherols and tocotrienols; 7.5 ml of Jason's Vitamin E oil (5,625 IU tocopheryl acetate) and Linoleate, with seven additional oils with possible activity similar to fish oil; the contents of 2 capsules of Omega 3 by Zone Perfect, Beverly, Mass., 320 mg eicosapentanoic acid (EPA) and 214 mg of docosahexaenoic acid (DHA). The ingredients are weighed and measured, combined, and gently mixed until a creamy consistency is obtained.

EXAMPLE 2

The following table relates to the various proportions of GLA, as well as DHA and EPA from molecularly distilled fish oil, within the scope of the invention:

TABLE 1

| GLA | EPA | DHA |
| --- | --- | --- |
| 20% | 40% | 40% |
| 10% | 40% | 50% |
| 30% | 50% | 20% |
| 15% | 40% | 45% |
| 15% | 55% | 30% |
| 10% | 30% | 60% |

EXAMPLE 3

The present example relates to the method of treatment of radiation dermatitis by topical application of the composition of the invention, as specifically described in EXAMPLE 1. Mrs. C had 30 sessions of radiation for breast cancer. Because she was fair-skinned and easily sunburned, Mrs. C used the cream with NAPCA and MSM immediately after her treatments and twice more each day. By the third day, a taped area of the breast, which did not receive the cream, exhibited blistering and burning. The remainder of the breast was not harmed. The tape was then removed and cream applied on the breast and underarm for the remainder of the treatments. After 30 treatments, the breast remained free of dermatitis and pigmentation changes and the underarm area remained free of dermatitis and became lightly tanned. The attending physician graded this level of protection as "extremely good" and attributed these results to the cream.

EXAMPLE 4

Mr. R went sunbathing in the lower latitudes, using the invention on one side of his hips and the carrier vehicle (cocoa butter cream) on the other. After one hour, the skin area treated with cocoa butter cream was intensely red and remained so for the next 48 hours. Half of the skin treated with the invention was white; the remaining half had a light pink color which faded within the next 12 hours. Mr. R is a golfer. He began using the invention for healing his resultant wind burn and now successfully uses the invention to prevent this type of trauma.

EXAMPLE 5

The present example relates to the method of reducing wrinkles by application of the composition of the invention, specifically as described in EXAMPLE 1. Mrs. C attempted to lose weight to reduce her risk of cancer recurrence. To prevent facial sagging and wrinkling, she applied the composition of the invention with NaPCA once at night. After losing 15% of her body weight, her forehead wrinkles were less prominent than before her weight reduction began.

EXAMPLE 6

This example relates to the method of treating thermal burns by the application of the composition of the invention.

Mrs. S spilled caramelized sugar on her forearm resulting in second degree burns which continued to ooze without healing for several days. A noticeable improvement was observed within hours of applying the cream described in

EXAMPLE 1

The following day, the oozing had stopped and most of the redness had disappeared, except for a small area that had been left untreated. New skin growth was rapid and without visible scarring.

EXAMPLE 7

This example relates to the method of treating dermatomyofibromas by application of the composition of the invention. Mrs. J had a ten year history of idiopathic dermatomyfibromas that first appeared on her legs and later appeared on her arms and hands, often after minor trauma, e.g., pet scratches. The lesions began as small, itchy blisters, that rapidly became indurated and scaled and did not heal. Prompt and repeated application of steroid cream or diphenhydramine (Benadryl®) cream as soon as a new lesion appeared occasionally produced healing, but many of the lesions required surgical removal. Application of the composition of the invention as specifically described in EXAMPLE 1 to a lesion several weeks old resulted in healing lesions that had been refractory to treatment with steroid or diphenhydramine.

I claim:

1. A composition effective for soothing traumatic conditions of the skin comprising:
   a. molecularly distilled omega-3 fish oils having a total weight of up to about 3000 mg, consisting of gamma-linoleic acid (GLA) in an amount ranging from about 10% to about 40% by weight, eicosapentanoic acid (EPA) in an amount ranging from about 20% to about 60% by weight, and docosahexaenoic acid (DHA) in an amount ranging from about 20% to about 60% by weight;
   b. mixed tocopherols in an amount of up to about 20,000 IU;
   c. lavender oil in an amount of up to about 1 mg;
   d. about 120 ml of a pharmaceutically acceptable carrier, the composition being active against traumatic conditions of the skin.

2. The composition according to claim 1 wherein the pharmaceutically acceptable carrier is cocoa butter.

3. The composition according to claim 1 wherein
   a. said molecularly distilled omega-3 fish oils are present in a total weight ranging from about 500 mg to about 2000 mg, said gamma-linoleic acid is present in an amount ranging from about 15% to about 30% by weight, said eicosapentanoic acid is present in an amount ranging from about 30% to about 50% by weight, and said docosahexaenoic acid is present in an amount ranging from about 30% to about 50% by weight;
   b. said tocopherol is present in an amount between about 1000 IU and about 15000 IU;
   c. said lavender oil is present in an amount up to about 600 mcg;
   d. about 120 ml of pharmaceutically acceptable carrier.

4. The composition according to claim 1 wherein:
   a. said molecularly distilled omega-3 fish oils are present in a total weight of about 1000 mg, said gamma-linoleic acid is present in an amount of about 20% by weight; said eicosapentanoic acid is present in an amount of about 40% by weight; said docosahexaenoic acid present in an amount of about 40% by weight;
   b. said tocopherol is present in an amount of about 5600 IU;
   c. said lavender oil is present in an amount of about 300 mcg;
   d. in about 120 ml of pharmaceutically acceptable carrier.

5. The composition according to claim 4 wherein the tocopherol is alpha-tocopheryl acetate and the pharmaceutically acceptable carrier is cocoa butter.

6. A composition effective for soothing traumatic conditions of the skin comprising:
   a. molecularly distilled omega-3 fish oils having a total weight of up to about 3000 mg, consisting of gamma-linoleic acid (GLA) in an amount ranging from about 10% to about 40% by weight, eicosapentanoic acid (EPA) in an amount ranging from about 20% to about 60% by weight, and docosahexaenoic acid (DHA) in an amount ranging from about 20% to about 60% by weight;
   b. mixed tocopherols in an amount of up to about 20,000 IU;
   c. lavender oil in an amount of up to about 1 mg;
   d. Sodium-PCA in an amount of up to about 1 g;
   e. about 120 ml of a pharmaceutically acceptable carrier, the composition being active against traumatic conditions of the skin.

7. The composition according to claim 6 wherein said Sodium PCA is present in an amount up to about 0.5 g.

8. The composition according to claim 7 wherein said Sodium PCA is present in an amount of about 0.25 g.

9. A composition effective for soothing traumatic conditions of the skin comprising:
   a. molecularly distilled omega-3 fish oils having a total weight of up to about 3000 mg, consisting of gamma-linoleic acid (GLA) in an amount ranging from about 10% to about 40% by weight, eicosapentanoic acid (EPA) in an amount ranging from about 20% to about 60% by weight, and docosahexaenoic acid (DHA) in an amount ranging from about 20% to about 60% by weight;
   b. mixed tocopherols in an amount of up to about 20,000 IU;
   c. lavender oil in an amount of up to about 1 mg;
   d. Methyl-Sulfonyl-Methane in an amount of about 6 g to about 18 g;
   e. about 120 ml of a pharmaceutically acceptable carrier, the composition being active against traumatic conditions of the skin.

10. The composition according to claim 9 wherein the Methyl-Sulfonyl-Methane is present in an amount of about 9 g to about 15 g.

11. The composition according to claim 9 wherein the Methyl-Sulfonyl-Methane is present in an amount of about 12 g.

12. A topically effective composition according to claim 1, characterized in that it is active against radiation dermatitis.

13. A topically effective composition according to claim 1, characterized in that it is active against exposure-induced wrinkles.

14. A topically effective composition according to claim 1, characterized in that it is active against thermal burns.

15. A topically effective composition according to claim 1, characterized in that it is active against sunburn.

16. The topically effective composition according to claim 1, characterized in that is active against dermatomyofibromas.

* * * * *